(12) United States Patent
Hosoya et al.

(10) Patent No.: US 8,217,094 B2
(45) Date of Patent: Jul. 10, 2012

(54) MONOLITH SEPARATION MEDIUM FOR CHROMATOGRAPHIC USE AND METHOD OF PRODUCING THE SAME

(75) Inventors: Ken Hosoya, Kyoto (JP); Mari Sakamoto, Miyagi (JP); Shigeyoshi Horiike, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 272 days.

(21) Appl. No.: 12/682,986

(22) PCT Filed: Oct. 17, 2007

(86) PCT No.: PCT/JP2007/070284
§ 371 (c)(1),
(2), (4) Date: Apr. 14, 2010

(87) PCT Pub. No.: WO2009/050801
PCT Pub. Date: Apr. 23, 2009

(65) Prior Publication Data
US 2010/0216906 A1    Aug. 26, 2010

(51) Int. Cl.
*C08J 9/00* (2006.01)
(52) U.S. Cl. .......... 521/178; 521/29; 521/155; 521/160; 521/179
(58) Field of Classification Search ............ 521/29, 521/155, 160, 178, 179
See application file for complete search history.

(56) References Cited

U.S. PATENT DOCUMENTS
7,473,367 B2 * 1/2009 Xie ............................. 210/635
7,955,504 B1 * 6/2011 Jovanovic et al. ....... 210/321.71

FOREIGN PATENT DOCUMENTS
WO WO-2004/070378 A1 8/2004
WO WO-2007/083348 A1 7/2007

OTHER PUBLICATIONS

International Search Report for the Application No. PCT/JP2007/070284 mailed Nov. 20, 2007.
Pflegerl, Karin et al., "Direct Synthesis of Peptides on Convective Interaction Media Monolithic Columns for Affinity Chromatography", Journal of Combinatorial Chemistry, 2002, vol. 4, No. 1, pp. 33-37.
Vlakh, E. et al., "Solid Phase Peptide Synthesis on Epoxy-Bearing Methacrylate Monoliths", Journal of Peptide Science, 2004, vol. 10, pp. 719-730.
Hosoya, Ken et al., "New Monolithic Chromatographic Materials Based on Organic Polymers", Chromatography, 2006, vol. 27, Supplement 2, pp. 55-56.
Kubo, Takuya et al., "Reproducibility of Polymer-based Monolithic Capillary Column", Chromatography, 2007, vol. 28, Supplement 1, pp. 45-46.

* cited by examiner

*Primary Examiner* — Irina S Zemel
(74) *Attorney, Agent, or Firm* — Cheng Law Group, PLLC

(57) ABSTRACT

A monolith separation medium comprising a skeletal phase and continuous pores forming a three-dimensional network structure, which has a functional group enabling the introduction of a new functional group on the surface of the skeletal phase. The skeletal phase has an average diameter of a submicron to micrometer size and is in a co-continuous structure of the non-particle-aggregation type. It is composed of an addition polymer of 1,3-bis(N,N'-diglycidylaminomethyl) cyclohexane as an epoxy compound with a bifunctional or higher amine compound, is rich in organic matters and is free from any aromatic-origin carbon atom. Thus, it is an organic polymer monolith separation medium of the non-particle-aggregation type.

9 Claims, 3 Drawing Sheets

MONOLITH SEPARATION MEDIUM FOR CHROMATOGRAPHIC USE AND METHOD OF PRODUCING THE SAME

TECHNICAL FIELD

The present invention relates to a monolith separation medium for chromatographic use which comprises a skeletal phase composed of an organic polymer, which has a three-dimensional network structure, interconnected pores, and a method of producing the same.

BACKGROUND ART

It is known that porous bodies for chromatographic use having both through-flow channels and a skeleton (referred to as "monoliths") have advantages which cannot be obtained by conventional particle-packed columns. For example, when such a porous body is used as a separation medium for HPLC, high column performance can be achieved due to its wide flow channels and thin skeleton and performance degradation can be reduced even at a high flow rate due to its low pressure loss. High-performance monoliths mainly made of silica gel have already been realized by microstructure control, and some of them are commercially available.

On the other hand, organic polymer monoliths are also known. Conventional organic polymer monoliths are formed by combinations of hydrophobic monomer components and poor solvents as pore-forming solvents (porogens). In a solution system containing a hydrophobic monomer component and a poor solvent, Van der Waals force between growing polymer chains becomes stronger than the steric hindrance of the polymer chains, and therefore the polymer chains aggregate. This causes nuclear formation due to the entanglement of the polymer chains, growth of microgel particles due to the aggregation of the polymer chains, and a rapid increase in the surface energy of the system. Further, the microgel particles aggregate and become coarse by similar growth (fractal growth) so that a gel is formed. In the case of such a solution system, gel formation is due to particle aggregation, and phase separation competes with gelation and occurs at a very early stage so that a monolithic structure with a small specific surface area is fixed. In this case, a particle-aggregation-type monolith is formed. Therefore, the conventional organic polymer monoliths do not have a skeletal structure and have a large pore tortuosity factor, and thus inherently have problems such as an increase in back pressure at a high flow rate and morphological change due to their compressibility.

Further, the conventional organic polymer monoliths also have a problem that when directly formed in empty column tubes with an inner diameter of 1 mm or more, they are peeled off from the column tubes due to their own compressibility. This makes it difficult to directly form organic polymer monoliths in empty column tubes.

In order to solve such problems, the present inventors have extensively studied, and as a result have developed a monolith separation medium whose skeletal phase is composed of an addition polymer of a bi- or higher-functional epoxy compound and a bi- or higher-functional amine compound, and has a functional group allowing a new functional group to be introduced thereinto (see Patent Document 1).

Further, another organic polymer monolith is also known, which has a skeletal phase composed of a copolymer of GMA (glycidyl methacrylate) and EDMA (ethylene dimethacrylate) and having amino groups introduced as functional groups by reacting epoxy groups present on the surface thereof with ethylenediamine (see Non-Patent Documents 1 and 2).

Patent Document 1: WO2007/083348 A1
Non-Patent Document 1: Journal of Peptide Science, Vol. 10, pp. 719-730, 2004
Non-Patent Document 2: Journal of Combinational Chemistry, Vol. 4, no. 1, pp. 33-37, 2002

DISCLOSURE OF THE INVENTION

Problem to be Solved by the Invention

It is an object of the present invention to provide a monolith separation medium whose skeletal phase is composed of an addition polymer of a bi- or higher-functional epoxy compound and a bi- or higher-functional amine compound, that is, a monolith separation medium having a skeletal phase which is similar to that of the monolith separation medium disclosed in Patent Document 1 and which is formed by a novel material combination.

Means for Solving the Problem

In order to achieve the above object, the present inventors have found that a porous body having a very uniform skeletal structure can be obtained by dissolving an epoxy compound having a specific molecular structure in a porogen, adding a bi- or higher-functional amine compound thereto, heating the solution to obtain a polymer, spinodally decomposing the porogen and the polymer, stably cross-linking the polymer before a non-particle-aggregation-type co-continuous structure of the polymer and the porogen transits to a particle aggregation structure due to the growth of phase separation to freeze the co-continuous structure, and removing the porogen. The epoxy compound having a specific molecular structure is 1,3-bis(N,N'-diglycidylaminomethyl)cyclohexane which is a liquid epoxy compound having four epoxy groups and which undergoes polymerization not at room temperature but at elevated temperatures.

The thus obtained organic polymer monolith separation medium according to the present invention comprises a skeletal phase, interconnected pores formed by a three-dimensional network of the skeletal phase, and a functional group present on the skeletal phase to allow a new functional group to be introduced into the skeletal phase, wherein the skeletal phase has an average diameter in submicron to micrometer size range and a non-particle-aggregation-type co-continuous structure, is composed of an addition polymer of 1,3-bis(N,N'-diglycidylaminomethyl)cyclohexane as an epoxy compound and a bi- or higher-functional amine compound, is rich in organic matter, and contains no aromatic-origin carbon atom or heterocyclic ring.

The term "functional group present on the skeletal phase to allow a new functional group to be introduced into the skeletal phase" includes a hydroxyl group generated by the reaction between an epoxy group and an amino group as well as remaining unreacted amino and epoxy groups.

The present invention also provides a method for producing the organic polymer monolith separation medium according to the present invention, the method comprising the steps of:

(A) heating 1,3-bis(N,N'-diglycidylaminomethyl)cyclohexane as an epoxy compound and a bi- or higher-functional amine compound in a porogen at a temperature in a range of 60 to 200° C. to polymerize the epoxy compound with the amine compound to obtain a gel; and (B) washing the gel with a solvent such as water to remove the porogen so that a skeletal phase remains.

The temperature of a polymerization reaction between the epoxy compound and the amine compound dissolved in the porogen is not particularly limited as long as it is suitable for the polymerization reaction to proceed, and is appropriately set depending on the kinds of epoxy compound, amine compound, and porogen to be used.

The amine compound is used as a curing agent. As the amine compound, a polyamine which is selected from the group consisting of aliphatic amines, alicyclic polyamines, and aliphatic polyamide amines, and which contains two or more primary amines can be used.

Examples of the aliphatic amines include ethylenediamine, diethylenetriamine, triethylenetetramine, tetraethylenepentamine, iminobispropylamine, bis(hexamethylene)triamine, 1,3,6-trisaminomethylhexane, polymethylenediamine, trimethylhexamethylenediamine, and polyetherdiamine and the like.

Examples of the alicyclic polyamines include isophoronediamine, menthanediamine, N-aminoethylpiperazine, 3,9-bis(3-aminopropyl) 2,4,8,10-tetraoxaspiron, bis(4-aminocyclohexyl)methane, and modified products thereof.

Examples of the aliphatic polyamide amines include those formed from polyamines and dimer acids.

Particularly preferred examples of the amine compound include bis(4-aminocyclohexyl)methane and bis(4-amino-3-methylcyclohexyl)methane.

The porogen refers to a solvent which can dissolve the epoxy compound and the curing agent as well as can cause reaction-induced phase separation after polymerization of the epoxy compound with the curing agent. Examples of such a porogen include cellosolves, esters, and glycols.

Examples of the cellosolves include methyl cellosolve and ethyl cellosolve.

Examples of the esters include ethylene glycol monomethyl ether acetate and propylene glycol monomethyl ether acetate and the like.

Examples of the glycols include polyethylene glycol and polypropylene glycol and the like.

Among these porogens, polyethylene glycols having a molecular weight of 600 or less are preferred, and polyethylene glycols having a molecular weight of 300 or less are particularly preferred.

According to the production method of the present invention, a suitable molar ratio between the epoxy compound and the amine compound used as raw materials is in the range of 1:1 to 1:3 (epoxy compound: amine compound).

A suitable amount of the porogen added is 1 to 99 wt % with respect to the total weight of the epoxy compound, the amine compound, and the porogen.

1,3-bis(N,N'-diglycidylaminomethyl)cyclohexane used in the present invention is a chiral compound having optical enantiomers, and may be either in racemic or optically active form.

The amine compound may also be a chiral compound. In this case, the amine compound may be either in racemic or optically active form.

An optical resolution separation medium for liquid chromatographic use intended to separate a racemic mixture into its S- and R-enantiomers can be realized when both the epoxy compound and the amine compound are optically active.

EFFECTS OF THE INVENTION

According to the present invention, a cross-linking reaction occurs before particle aggregation occurs, which makes it possible to realize an organic polymer monolith having a clear skeletal phase and a co-continuous structure. Further, the cross-linking reaction easily occurs due to the use of a polyfunctional epoxy compound, and therefore it is expected that the shrinkage of the organic polymer monolith due to the cross-linking reaction will be reduced. Particularly, 1,3-bis(N,N'-diglycidylaminomethyl)cyclohexane as an epoxy compound is liquid and poorly reactive at room temperature, and therefore can be more easily injected into a column or the like as compared to an epoxy compound which needs to be dissolved in a porogen at an elevated temperature, such as a solid epoxy compound. Further, 1,3-bis(N,N'-diglycidylaminomethyl)cyclohexane is a tetrafunctional epoxy compound, which makes it possible to reduce shrinkage during cross-linking and gelation which occur after phase separation.

As described above, the monolith separation medium according to the present invention has a skeletal phase which has an average diameter in submicron to micrometer size range and a non-particle-aggregation-type co-continuous structure, and which is composed of an addition polymer of a bi- or higher-functional epoxy compound and a bi- or higher-functional amine compound, and which is rich in organic matter, and which contains no aromatic-origin carbon atom, and is therefore useful as a stationary phase for liquid chromatographic use and achieves high performance which cannot be achieved by conventional monolith separation media at all. Further, the monolith separation medium according to the present invention can be used in various-sized columns ranging from capillary columns to general-purpose columns.

According to the production method of the present invention, a monolith separation medium can be very easily produced by heating an epoxy compound and an amine compound in a porogen to polymerize the epoxy compound with the amine compound. Therefore, the production method according to the present invention can be effectively used to produce various-sized columns ranging from capillary columns to columns having a relatively large diameter.

DETAILED DESCRIPTION OF THE INVENTION

A separation medium according to the present invention is a high-performance and non-particle-aggregation-type polymer monolith separation medium formed by a specific material combination of 1,3-bis(N,N'-diglycidylaminomethyl)cyclohexane as an epoxy compound and a curing agent. More specifically, the epoxy compound, that is, 1,3-bis(N,N'-diglycidylaminomethyl)cyclohexane is a tetrafunctional non-aromatic epoxy compound, and the curing agent is a bi- or higher-functional non-aromatic amine compound. Such a material combination makes it possible to obtain a high-performance and non-particle-aggregation-type polymer monolith separation medium having a three-dimensional branching structure.

Hereinbelow, an epoxy compound and a curing agent which can be used in the present invention will be exemplified.

EXAMPLES

Example 1

A separation medium according to the present invention and a method suitable for producing the same will be described with reference to Example 1. In Example 1, 1,3-bis(N,N'-diglycidylaminomethyl)cyclohexane (BDAC) was used as an epoxy compound, bis(4-aminocyclohexyl) methane (BACM) was used as an amino compound, and polyethylene glycol with a molecular weight of 300 (manufactured by Nacalai Tesque Inc. under the trade name of "PEG300") was used as a porogen. The 1,3-bis(N,N'-diglycidylaminomethyl)cyclohexane may be either in racemic or optically active form. The BDAC and BACM have the following chemical structural formulas.

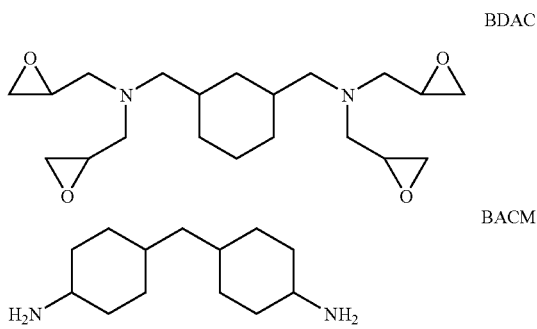

BDAC

BACM (Production of Polymer Monolith)

0.93 g of the BDAC, 0.47 g of the BACM, and 3.6 g of the PEG300 were prepared, injected into a fused quartz capillary tube at room temperature, and heated in an oil bath at 150° C. for 24 hours to polymerize the BDAC with the BACM. After the completion of the polymerization, an obtained gel was washed with methanol and water.

Figure 1:
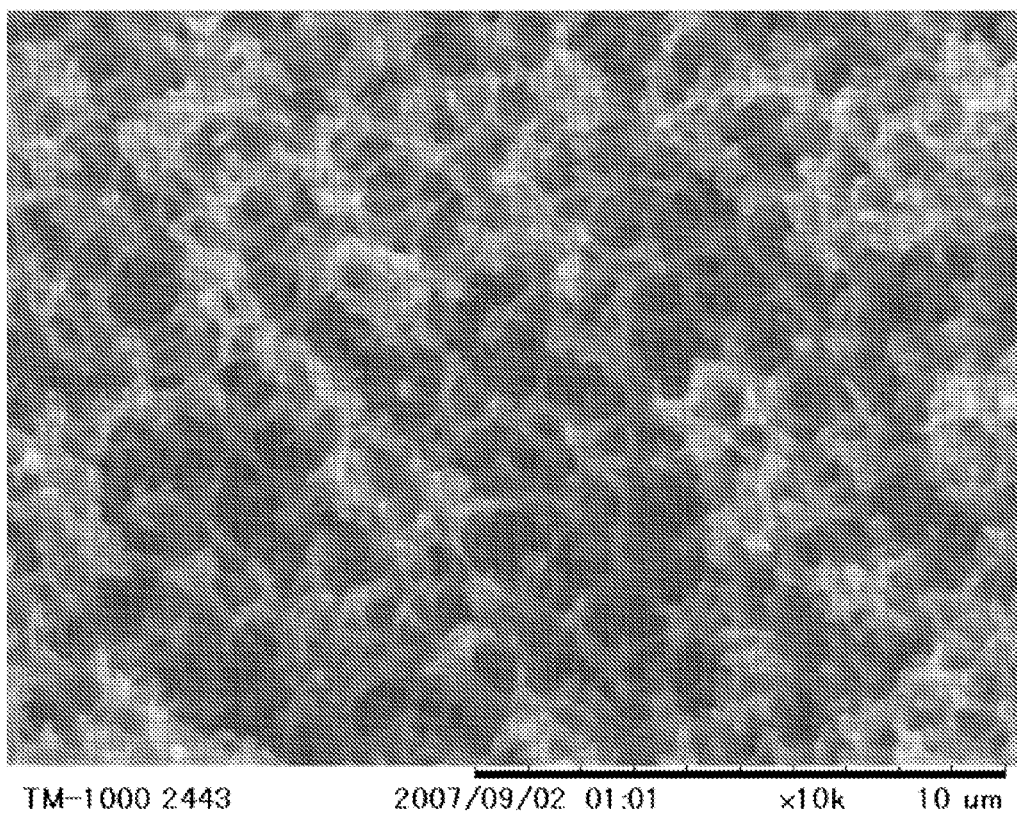
FIG. 1 is a scanning electron microscope image of an organic polymer monolith capillary column produced in Example 1.

FIG. 1 is a scanning electron micrograph of a capillary column filled with an organic polymer monolith produced by polymerization in Example 1. As can be seen from FIG. 1, the organic polymer monolith has a skeletal phase having a micrometer-sized average diameter and a non-particle-aggregation-type co-continuous structure and pores formed by a three-dimensional network structure of the skeletal phase.

Figure 2:
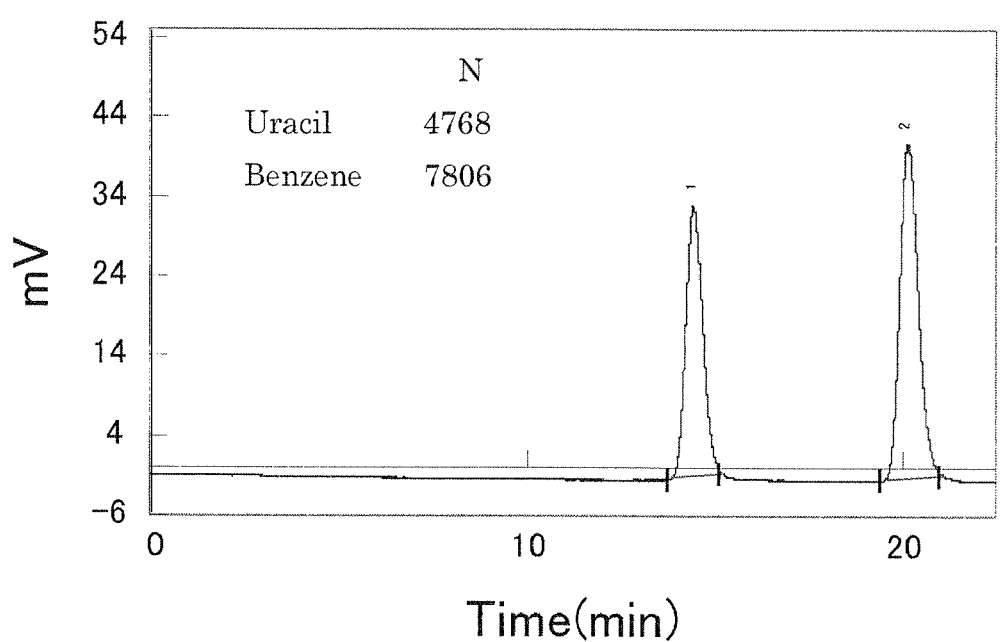
FIG. 2 is a chromatogram showing separation of uracil and benzene using the capillary column shown in FIG. 1.

Separation of uracil and benzene was performed using the organic polymer monolith capillary column (inner diameter: 100 µm, length: 20 cm) produced in Example 1. FIG. 2 is a chromatogram showing separation of uracil and benzene. As a mobile phase, a 60% aqueous acetonitrile solution (pH 7.0 adjusted by 20 mM phosphate buffer) was used. The temperature of the capillary column was room temperature. Detection was carried out by measuring ultraviolet absorption at 210 nm. In FIG. 2, the former peak is assigned to uracil, the latter peak is assigned to benzene, and N represents the number of theoretical plates.

The number of theoretical plates was calculated by the half-height width method using the following formula:

$$N = 5.54 (t_r / W_{0.5h})^2$$

where $t_r$ represents retention time and $W_{0.5h}$ represents a peak width at half-height.

Comparative Example

As an epoxy compound, 2-[(4-{1-methyl-1-[4-(2oxiranylmethoxy)phenyl]ethyl}phenoxy)meth yl]oxirane (BADE) being an aromatic compound was used. As an amine compound, BACM, which was the same as that used in Example 1, was used. As a porogen, polyethylene glycol with a molecular weight of 200 (manufactured by Nacalai Tesque Inc. under the trade name of "PEG200") was used.

0.52 g of the BACM was melted in 7.20 g of the PEG200 by heating, and then 2.33 g of the BADE was added thereto and mixed by stirring. The thus obtained solution was injected into a fused quartz capillary tube and heated in an oven at 120° C. for 1 hour to polymerize the BADE with the BACM.

After the completion of the polymerization, an obtained gel was washed with water and methanol and then vacuum-dried.

Figure 3:
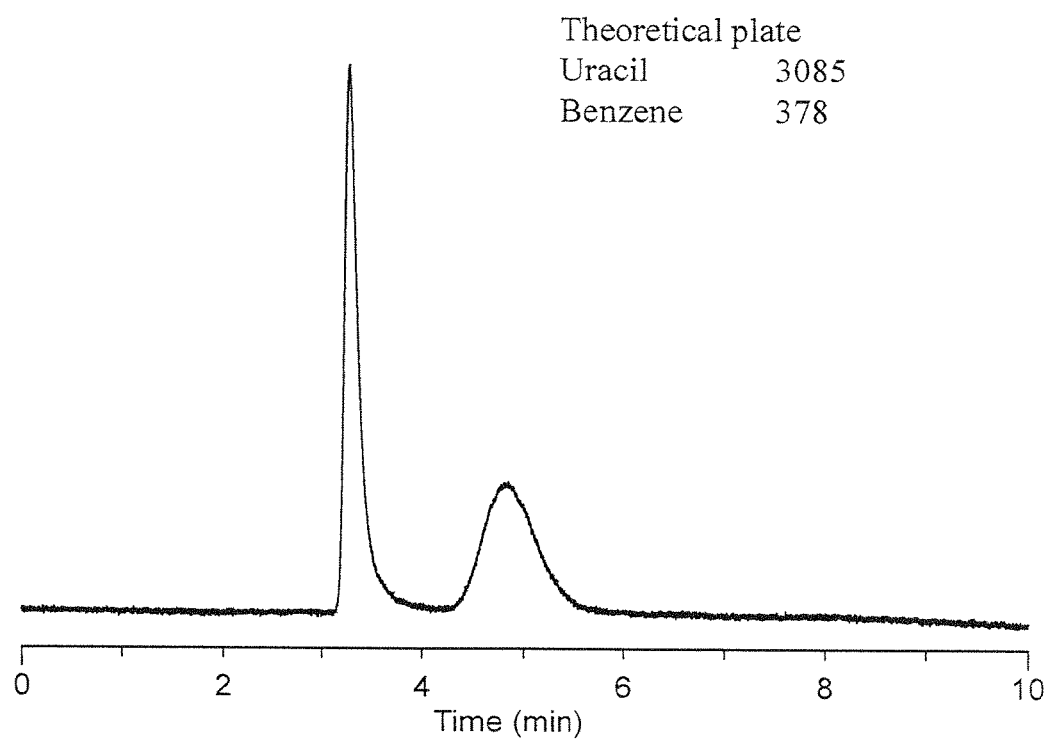
FIG. 3 is a chromatogram showing separation of uracil and benzene using an organic polymer monolith capillary column produced in Comparative Example.

Separation of uracil and benzene was performed using an organic polymer monolith capillary column (inner diameter: 100 µm, length: 20 cm) produced in Comparative Example. FIG. 3 is a chromatogram showing separation of uracil and benzene. As a mobile phase, a 60% aqueous acetonitrile solution (pH 7.0 adjusted by 20 mM phosphate buffer) was used. The temperature of the capillary column was room temperature, the flow rate of the mobile phase was 0.15 mL/min, the linear velocity was 1.01 mm/sec, and the pressure was 50 kg/cm². Detection was carried out by measuring ultraviolet absorption at 210 nm in a capillary tube with an inner diameter of 50 µm placed 9 cm away from the column.

In FIG. 3, the former peak is assigned to uracil and the latter peak is assigned to benzene. The number of theoretical plates for uracil and benzene calculated by the half-height width method were 3085 and 378, respectively, which were lower than those of the organic polymer monolith capillary column according to the present invention produced in Example 1. The reason for this can be considered as follows: the epoxy compound used in Comparative Example is an aromatic compound, and therefore, a formed skeletal phase contains aromatic-origin carbon atoms.

Industrial Applicability

The monolith separation medium according to the present invention can be used as a stationary phase in various-sized liquid chromatographic columns ranging from capillary columns to general-purpose columns.

What is claimed is:

1. An organic polymer gel monolith separation medium for chromatographic use comprising:
   a skeletal phase;
   interconnected pores formed by a three-dimensional network of the skeletal phase; and
   a functional group present on the skeletal phase to allow a new functional group to be introduced into the skeletal phase,
   wherein the skeletal phase has an average diameter in submicron to micrometer size range and a non-particle-aggregation-type co-continuous structure, is composed of an addition polymer of 1,3-bis(N,N'-diglycidylaminomethyl)cyclohexane as an epoxy compound and a bi- or higher-functional amine compound, is rich in organic matter, and contains no aromatic-origin carbon atom or heterocyclic ring.

2. The monolith separation medium according to claim 1, wherein the amine compound is a polyamine, which is selected from the group consisting of aliphatic amines, alicyclic polyamines, and aliphatic polyamide amines, and which contains two or more primary amines.

3. The monolith separation medium according to claim 2, wherein the amine compound is bis(4-aminocyclohexyl) methane as an alicyclic polyamine.

4. The monolith separation medium according to claim 1, wherein the epoxy compound and the amine compound are both optically active to allow optical enantiomers to be separated from each other.

5. A method of producing the monolith separation medium according to claim 1, comprising the steps of:
(A) heating 1,3-bis(N,N'-diglycidylaminomethyl)cyclohexane as an epoxy compound and a bi- or higher-functional amine compound in a porogen at a temperature in a range of 60 to 200° C. to polymerize the epoxy compound with the amine compound to obtain a gel; and
(B) washing the gel with a solvent to remove the porogen so that a skeletal phase remains.

6. The production method according to claim 5, wherein the amine compound is an aliphatic amine, an alicyclic polyamine, or an aliphatic polyamide amine.

7. The production method according to claim 6, wherein the amine compound is bis(4-aminocyclohexyl)methane as an alicyclic polyamine.

8. The production method according to claim 5, wherein the porogen is a cellosolve, an ester, or a glycol.

9. The production method according to claim 8, wherein the porogen is polyethylene glycol.

* * * * *